US010493225B2

(12) United States Patent
Thiessen (10) Patent No.: US 10,493,225 B2
(45) Date of Patent: Dec. 3, 2019

(54) SAFE STANDBY MODE FOR VENTILATOR (71) Applicant: Covidien LP, Mansfield, MA (US)

(72) Inventor: Ron Thiessen, Maple Ridge (CA)

(73) Assignee: Covidien LP, Mansfield, MA (US)

( * ) Notice: Subject to any disclaimer, the term of this patent is extended or adjusted under 35 U.S.C. 154(b) by 808 days.

(21) Appl. No.: 15/170,405

(22) Filed: Jun. 1, 2016

(65) Prior Publication Data
US 2016/0354566 A1 Dec. 8, 2016

Related U.S. Application Data (63) Continuation of application No. 13/618,359, filed on Sep. 14, 2012, now Pat. No. 9,381,314, which is a continuation of application No. 12/236,127, filed on Sep. 23, 2008, now Pat. No. 8,424,520.

(51) Int. Cl.
*A61M 16/00* (2006.01)
*A61M 16/20* (2006.01)
*A61M 16/08* (2006.01)

(52) U.S. Cl.
CPC .... *A61M 16/0051* (2013.01); *A61M 16/0057* (2013.01); *A61M 16/024* (2017.08); *A61M 16/201* (2014.02); *A61M 16/0833* (2014.02); *A61M 2016/003* (2013.01); *A61M 2016/0027* (2013.01); *A61M 2205/13* (2013.01); *A61M 2205/14* (2013.01); *A61M 2205/18* (2013.01); *A61M 2205/33* (2013.01); *A61M 2205/3334* (2013.01); *A61M 2205/502* (2013.01); *A61M 2205/505* (2013.01)

(58) Field of Classification Search
CPC ....... A61M 16/0051; A61M 2016/0015–0024; A61M 2205/13; A61M 2205/14; A61M 2205/18; A61M 2205/33; A61M 2205/502
See application file for complete search history.

(56) References Cited

U.S. PATENT DOCUMENTS

| 4,340,044 A | * | 7/1982 | Levy | ................... | A61M 16/024 |
| | | | | | 128/204.21 |
| 4,550,726 A | | 11/1985 | McEwen | | |
| 4,752,089 A | | 6/1988 | Carter | | |
| 4,921,642 A | | 5/1990 | LaTorraca | | |

(Continued)

FOREIGN PATENT DOCUMENTS

| EP | 0392503 | 10/1990 |
| EP | 0459647 | 4/1991 |

(Continued)

OTHER PUBLICATIONS

"Breath of Fresh Air", *Health Devices*, Dec. 2011, 2011 ECRI Institute, pp. 398-406.

(Continued)

*Primary Examiner* — Valerie L Woodward (57) ABSTRACT

A ventilator with a safe standby mode is provided. The safe standby mode allows a user to disconnect a patient from the ventilator, without the ventilator generating alarms and while maintaining previously entered ventilation parameters. In addition, while in the safe standby mode, a patient connection status is monitored, and a ventilation mode is entered automatically if the ventilator determines that a patient is connected to the ventilator while the ventilator is in the safe standby mode.

20 Claims, 4 Drawing Sheets

(56) References Cited

U.S. PATENT DOCUMENTS

| | | | |
|---|---|---|---|
| 4,954,799 A | 9/1990 | Kumar | |
| 5,057,822 A | 10/1991 | Hoffman | |
| 5,072,737 A | 12/1991 | Goulding | |
| 5,094,246 A | 3/1992 | Rusz et al. | |
| 5,150,291 A | 9/1992 | Cummings et al. | |
| 5,161,525 A | 11/1992 | Kimm et al. | |
| 5,226,416 A * | 7/1993 | Bethune | A61B 5/0205 340/573.1 |
| 5,237,987 A | 8/1993 | Anderson et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,319,540 A | 6/1994 | Isaza et al. | |
| 5,325,861 A | 7/1994 | Goulding | |
| 5,333,606 A | 8/1994 | Schneider et al. | |
| 5,339,807 A | 8/1994 | Carter | |
| 5,343,857 A | 9/1994 | Schneider et al. | |
| 5,351,522 A | 10/1994 | Lura | |
| 5,357,946 A | 10/1994 | Kee et al. | |
| 5,368,019 A | 11/1994 | LaTorraca | |
| 5,383,449 A | 1/1995 | Forare et al. | |
| 5,385,142 A | 1/1995 | Brady et al. | |
| 5,390,666 A | 2/1995 | Kimm et al. | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,503,146 A * | 4/1996 | Froehlich | A61M 16/024 128/202.22 |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,542,415 A | 8/1996 | Brady | |
| 5,544,674 A | 8/1996 | Kelly | |
| 5,549,106 A | 8/1996 | Gruenke et al. | |
| 5,596,984 A | 1/1997 | O'Mahoney et al. | |
| 5,630,411 A | 5/1997 | Holscher | |
| 5,632,270 A | 5/1997 | O'Mahony et al. | |
| 5,645,048 A | 7/1997 | Brodsky et al. | |
| 5,660,171 A | 8/1997 | Kimm et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,715,812 A | 2/1998 | Deighan et al. | |
| 5,762,480 A | 6/1998 | Adahan | |
| 5,771,884 A | 6/1998 | Yarnall et al. | |
| 5,791,339 A | 8/1998 | Winter | |
| 5,794,986 A | 8/1998 | Gansel et al. | |
| 5,813,399 A | 9/1998 | Isaza et al. | |
| 5,826,575 A | 10/1998 | Lall | |
| 5,829,441 A | 11/1998 | Kidd et al. | |
| 5,864,938 A | 2/1999 | Gansel et al. | |
| 5,865,168 A | 2/1999 | Isaza | |
| 5,881,717 A * | 3/1999 | Isaza | A61M 16/0051 128/202.22 |
| 5,881,723 A | 3/1999 | Wallace et al. | |
| 5,884,623 A | 3/1999 | Winter | |
| 5,909,731 A | 6/1999 | O'Mahoney et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,934,274 A | 8/1999 | Merrick et al. | |
| 6,024,089 A | 2/2000 | Wallace et al. | |
| 6,041,780 A | 3/2000 | Richard et al. | |
| 6,047,860 A | 4/2000 | Sanders | |
| 6,076,523 A | 6/2000 | Jones et al. | |
| 6,102,038 A | 8/2000 | DeVries | |
| 6,116,240 A | 9/2000 | Merrick et al. | |
| 6,116,464 A | 9/2000 | Sanders | |
| 6,123,073 A | 9/2000 | Schlawin et al. | |
| 6,135,106 A | 10/2000 | Dirks et al. | |
| 6,142,150 A | 11/2000 | O'Mahoney et al. | |
| 6,158,433 A | 12/2000 | Ong et al. | |
| 6,161,539 A | 12/2000 | Winter | |
| 6,220,245 B1 | 4/2001 | Takabayashi et al. | |
| 6,230,708 B1 | 5/2001 | Radko | |
| 6,269,812 B1 | 8/2001 | Wallace et al. | |
| 6,273,444 B1 | 8/2001 | Power | |
| 6,283,119 B1 | 9/2001 | Bourdon | |
| 6,305,373 B1 | 10/2001 | Wallace et al. | |
| 6,321,748 B1 | 11/2001 | O'Mahoney | |
| 6,325,785 B1 | 12/2001 | Babkes et al. | |
| 6,357,438 B1 | 3/2002 | Hansen | |
| 6,360,745 B1 | 3/2002 | Wallace et al. | |
| 6,369,838 B1 | 4/2002 | Wallace et al. | |
| 6,412,483 B1 | 7/2002 | Jones et al. | |
| 6,439,229 B1 | 8/2002 | Du et al. | |
| 6,467,478 B1 | 10/2002 | Merrick et al. | |
| 6,546,930 B1 | 4/2003 | Emerson et al. | |
| 6,553,991 B1 | 4/2003 | Isaza | |
| 6,557,553 B1 | 5/2003 | Borrello | |
| 6,571,622 B2 | 6/2003 | Koch | |
| 6,571,795 B2 | 6/2003 | Bourdon | |
| 6,622,726 B1 | 9/2003 | Du | |
| 6,644,310 B1 | 11/2003 | Delache et al. | |
| 6,668,824 B1 | 12/2003 | Isaza et al. | |
| 6,675,801 B2 | 1/2004 | Wallace et al. | |
| 6,718,974 B1 | 4/2004 | Moberg | |
| 6,725,447 B1 | 4/2004 | Gilman et al. | |
| 6,739,337 B2 | 5/2004 | Isaza | |
| 6,761,167 B1 | 7/2004 | Nadjafizadeh et al. | |
| 6,761,168 B1 | 7/2004 | Nadjafizadeh et al. | |
| 6,814,074 B1 | 11/2004 | Nadjafizadeh et al. | |
| 6,820,618 B2 | 11/2004 | Banner et al. | |
| 6,866,040 B1 | 3/2005 | Bourdon | |
| 6,960,854 B2 | 11/2005 | Nadjafizadeh et al. | |
| 7,036,504 B2 | 5/2006 | Wallace et al. | |
| 7,077,131 B2 | 7/2006 | Hansen | |
| RE39,225 E | 8/2006 | Isaza et al. | |
| 7,117,438 B2 | 10/2006 | Wallace et al. | |
| 7,188,621 B2 | 3/2007 | DeVries et al. | |
| 7,222,623 B2 | 5/2007 | DeVries et al. | |
| 7,270,126 B2 | 9/2007 | Wallace et al. | |
| 7,369,757 B2 | 5/2008 | Farbarik | |
| 7,370,650 B2 | 5/2008 | Nadjafizadeh et al. | |
| 7,428,902 B2 | 9/2008 | Du et al. | |
| 7,460,959 B2 | 12/2008 | Jafari | |
| 7,487,773 B2 | 2/2009 | Li | |
| 7,654,802 B2 | 2/2010 | Crawfor, Jr. et al. | |
| 7,694,677 B2 | 4/2010 | Tang | |
| 7,717,113 B2 | 5/2010 | Andrieux | |
| D618,356 S | 6/2010 | Ross | |
| 7,784,461 B2 | 8/2010 | Figueiredo et al. | |
| 7,823,588 B2 | 11/2010 | Hansen | |
| 7,855,716 B2 | 12/2010 | McCreary et al. | |
| D632,796 S | 2/2011 | Ross et al. | |
| D632,797 S | 2/2011 | Ross et al. | |
| 7,891,354 B2 | 2/2011 | Farbarik | |
| 7,893,560 B2 | 2/2011 | Carter | |
| D638,852 S | 5/2011 | Skidmore et al. | |
| 7,984,714 B2 | 7/2011 | Hausmann et al. | |
| D643,535 S | 8/2011 | Ross et al. | |
| 7,992,557 B2 | 8/2011 | Nadjafizadeh et al. | |
| 8,001,967 B2 | 8/2011 | Wallace et al. | |
| D645,158 S | 9/2011 | Sanchez et al. | |
| 8,021,310 B2 | 9/2011 | Sanborn et al. | |
| D649,157 S | 11/2011 | Skidmore et al. | |
| D652,521 S | 1/2012 | Ross et al. | |
| D652,936 S | 1/2012 | Ross et al. | |
| D653,749 S | 2/2012 | Winter et al. | |
| 8,113,062 B2 | 2/2012 | Graboi et al. | |
| D655,405 S | 3/2012 | Winter et al. | |
| D655,809 S | 3/2012 | Winter et al. | |
| D656,237 S | 3/2012 | Sanchez et al. | |
| 8,181,648 B2 | 5/2012 | Perine et al. | |

(56) References Cited

U.S. PATENT DOCUMENTS

| | | |
|---|---|---|
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,424,520 B2 | 4/2013 | Thiessen |
| 9,381,314 B2 | 7/2016 | Thiessen |
| 2003/0111078 A1 | 6/2003 | Habashi |
| 2005/0039748 A1 | 2/2005 | Andrieux |
| 2005/0061321 A1 | 3/2005 | Jones |
| 2005/0115564 A1 | 6/2005 | DeVries et al. |
| 2005/0139212 A1 | 6/2005 | Bourdon |
| 2007/0017515 A1 | 1/2007 | Wallace et al. |
| 2007/0077200 A1 | 4/2007 | Baker |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0053441 A1 | 3/2008 | Gottlib et al. |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2009/0038616 A1 | 2/2009 | Mulcahy et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1 | 8/2009 | Vandine et al. |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0282259 A1 | 11/2010 | Figueiredo et al. |
| 2010/0288283 A1 | 11/2010 | Campbell et al. |
| 2010/0300446 A1 | 12/2010 | Nicolazzi et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |

(56) References Cited

U.S. PATENT DOCUMENTS

2013/0025596 A1 1/2013 Jafari et al.
2013/0025597 A1 1/2013 Doyle et al.

FOREIGN PATENT DOCUMENTS

| EP | 0722747 | 7/1996 |
|---|---|---|
| WO | WO 2008/008163 | 1/2008 |
| WO | WO 2009/059359 | 5/2009 |

OTHER PUBLICATIONS

7200 Series Ventilator, Options, and Accessories: Operator's Manual. Nellcor Puritan Bennett, Part No. 22300 A, Sep. 1990, pp. 1-196.
7200 Ventilatory System: Addendum/Errata. Nellcor Puritan Bennett, Part No. 4-023576-00, Rev. A, Apr. 1988, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Avance, GE Healthcare, available at http://www.instrumentarium.com/usen/anesthesia/docs/an4583a.pdf, Document No. AN-0105, Apr. 2006, pp. 1-8.
Centiva/5 Critical Care Ventilator, GE Healthcare, available at http://www.berkeley-medical.com.br/imagens/produtos/2.pdf, Document No. CC3657-E, Sep. 2005, pp. 1-8.
Centiva/5 Critical Care Ventilator, GE Healthcare, Document No. CC3662-C, Oct. 2005, pp. 1-8.
Critical Care Therapy and Respiratory Care Section, National Institutes of Health, Warren G. Magnuson Clinical Center, Critical Care Medicine Department, available at: http://clinicalcenter.nih.gov/ccmd/cctrcs/pdCdocs/Clinical% 020Monitoring/10-cp-100% 20pulmonary%20mon.pdf, Mar. 2000, pp. 1-7.
Datex-Ohmeda Output Protocols, Datex-Ohmeda Inc., Version 1.5, Aug. 14, 2001, pp. 1-31.
DRAGER Medical, Evita Infinity V500 Ventilation Unit, Instructions for Use, Infinity Acute Care System, Feb. 2011, 3 pgs.
GE Healthcare, "Centiva/5: Critical Care Ventilator", Sep. 2005, 8 pages.
James A. McEwen PHD, Carolyn F. Small PHD, Leonard C. Jenkins MD, Detection of interruptions in the breathing gas of ventilated anaesthetized patients, Canadian Journal of Anaesthesia, 1988, pp. 549-561.
Luis Rivera, MD and Charles Weissman, MD, Dynamic Ventilatory Characteristics During Weaning in Postoperative Critically Ill Patients, Critical Care and Trauma, Respiratory Patterns and Weaning, International Anesthesia Research Society, 1997, pp. 1250-1255.
McPherson, Steven P., "Respiratory Therapy Equipment" $4^{th}$ Edition, the C.V. Mosby Company, St. Louis, MO, 1990, p. 336, 3 pages total.
PCT International Search Report and Written Opinion in Application PCT/US/2009/057871, dated Apr. 12, 2009, 9 pgs.
Product Comparison Ventilators, Intensive Care, hpcs, ECRI, Apr. 2006, pp. 1-71.
U.S. Appl. No. 12/236,127, Notice of Allowance dated Dec. 24, 2012, 5 pgs.
U.S. Appl. No. 12/236,127, Notice of Allowance dated Mar. 18, 2013, 2 pgs.
U.S. Appl. No. 12/236,127, Notice of Allowance dated Jul. 25, 2012, 8 pgs.
U.S. Appl. No. 12/236,127, Notice of Allowance dated Sep. 18, 2012, 5 pgs.
U.S. Appl. No. 12/236,127, Office Action dated Feb. 1, 2012, 15 pgs.
U.S. Appl. No. 12/236,127, Office Action dated Aug. 22, 2011, 10 pgs.
VentWorld Ventilator Product Booth, Bear 1 Ventilator, found online May 9, 2012 at: http://www.ventworld.com/equipment/Prodbooth.asp?ProdId=113, 3 pgs.

* cited by examiner

SAFE STANDBY MODE FOR VENTILATOR

CROSS-REFERENCE TO RELATED APPLICATIONS

This application is a continuation application of U.S. patent application Ser. No. 13/618,359, entitled "SAFE STANDBY MODE FOR VENTILATOR," filed on Sep. 14, 2012, which application is a continuation application of U.S. patent application Ser. No. 12/236,127 (now U.S. Pat. No. 8,424,520), filed on Sep. 23, 2008, the entire disclosures of which are hereby incorporated herein by reference.

FIELD OF THE INVENTION

The present invention is generally directed to a safe standby mode for a ventilator.

BACKGROUND

Ventilators are used to provide a breathing gas to a patient who is unable to breathe sufficiently without assistance. In modern medical facilities, pressurized air and oxygen sources are often available from wall outlets. Accordingly, ventilators may provide pressure regulating valves connected to centralized sources of pressurized air and pressurized oxygen. The pressure regulating valves function to regulate flow so that respiratory air having a desired concentration of oxygen is supplied to the patient at desired pressures and rates. Ventilators capable of operating independently of external sources of pressurized air and oxygen are also available.

A typical ventilator has a number of settings that can be used to control parameters according to which breathing gas is supplied to a patient. In order to facilitate the entry of ventilator settings by a user, some ventilators have provided a standby mode. In a conventional standby mode, a user may set operating parameters, without breathing gas being provided at the supply port of the ventilator. Accordingly, in order to provide breathing gas to a patient, the user must remember to exit the standby mode and enter a normal operating mode. If this is not done, no benefit is provided to the patient, as no breathing gas is supplied in a conventional standby mode. Accordingly, such standby modes may be considered unsafe, as the ventilator may appear to be on, even though no breathing gas is being supplied to the patient.

After ventilation of a patient has begun, a disconnect mode can be entered if the ventilator determines that the patient has become disconnected. In the disconnect mode, an alarm will typically sound if the disconnect state has persisted for some threshold period of time. Because of this, a medical professional may need to repeatedly silence the disconnect alarm, for example while performing procedures that require the disconnection of the patient from the ventilator. Moreover, in such situations, turning off the ventilator is not an attractive option, because there typically is a ventilator boot time or delay between powering on the ventilator and obtaining a breathing gas from the ventilator. In addition, patient settings will typically need to be reentered after the ventilator has been powered off. Although some ventilators provide the option of entering a standby mode during procedures that require disconnecting the patient, the use of such a conventional standby mode is not particularly safe. In particular, no breathing gas is supplied to the patient if the user forgets to restart normal ventilation after entering the standby mode, even if the patient is connected to the ventilator.

SUMMARY

Ventilators with safe standby modes are provided. In some embodiments, a ventilation mode providing breathing gas to a patient is entered in response to determining that the ventilator is connected to a patient while in the safe standby mode. In accordance with some embodiments of the present invention, the ventilator can also provide a prompt to a user that allows the user to select entry into the safe standby mode upon the ventilator determining that the patient has become disconnected from the ventilator. In accordance with other embodiments of the present invention, a user may be offered an option of selecting a safe standby mode while the ventilator is in a normal ventilation mode.

More particularly, in response to detecting that a patient has become disconnected from the ventilator while the ventilator is in a normal ventilation mode, the ventilator enters a disconnect mode. In the disconnect mode, an alarm is periodically generated if the disconnect status is not resolved, for example by reconnecting the patient to the ventilator or powering off the ventilator. In the disconnect mode, embodiments of the present invention allow the user to select the safe standby mode. In the safe standby mode, an alarm is not periodically generated, and the ventilator may remain in the safe standby mode indefinitely. In addition, embodiments of the present invention monitor a connection status of the patient while the ventilator is in the safe standby mode. If the ventilator determines that the patient has been connected to the ventilator while in a safe standby mode, a normal ventilation mode in which breathing gas is supplied to the patient is entered automatically.

In accordance with further embodiments of the present invention, a user may select the safe standby mode while the ventilator is in the normal ventilation mode. In response to a selection of the safe standby mode, the ventilator may output a message to the user requesting that the user confirm entry into the safe standby mode, and indicating that a specified period of time will be allowed for completing patient disconnection. After receiving confirmation from the user that the safe standby mode is to be entered, a countdown to the specified or defined period of time may be output. If the user completes patient disconnection within the defined period of time, the safe standby mode is entered. After entering the standby mode, if the ventilator then determines that the patient has been reconnected to the ventilator, normal ventilation resumes. Also, if the user does not successfully disconnect the patient within the defined period of time, normal ventilation is continued. In accordance with further embodiments of the present invention, following a failure to disconnect the patient within the defined period of time, another opportunity to confirm entry into the safe standby mode is presented, together with a notification of the defined period of time in which disconnection will need to be completed.

Additional features and advantages of embodiments of the present invention will become more readily apparent from the following description, particularly when taken together with the accompanying drawings.

DETAILED DESCRIPTION

Figure 1:
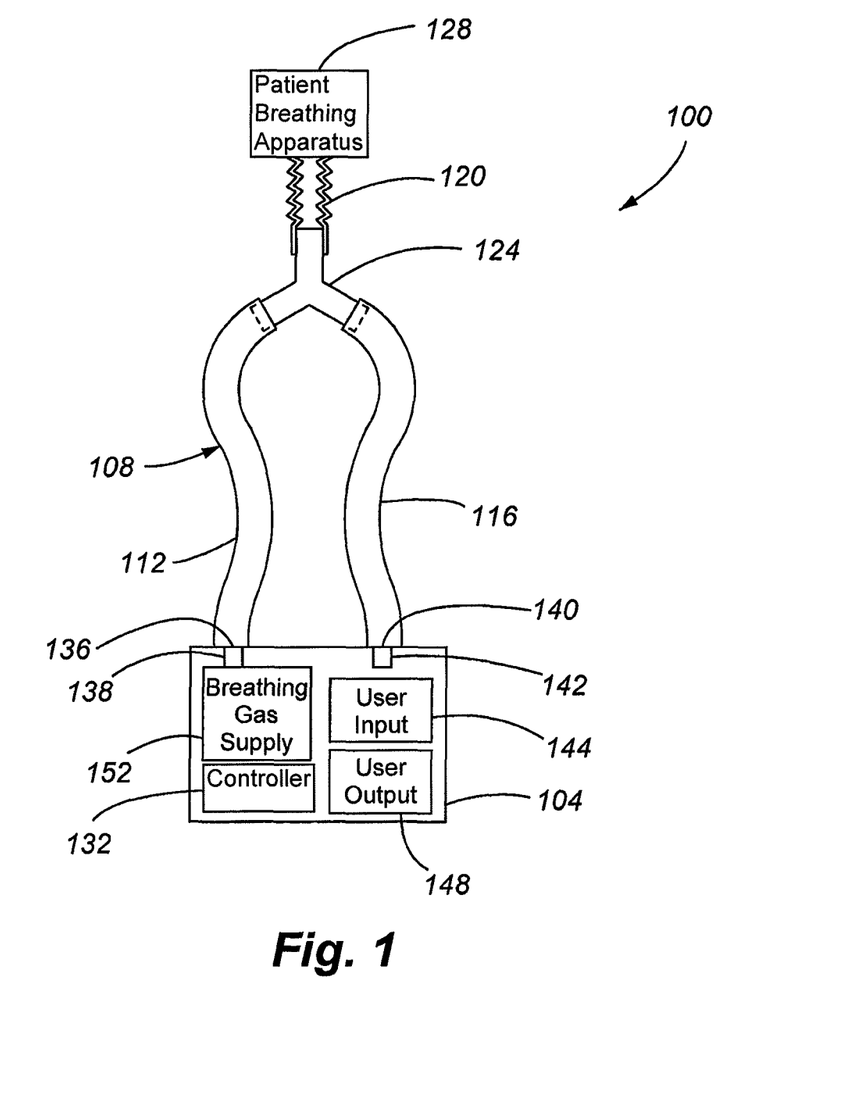
FIG. 1 is a depiction of a ventilation system in accordance with embodiments of the present invention.

FIG. 1 is a depiction of a ventilation system 100 in accordance with embodiments of the present invention. In general, the system 100 includes a ventilator 104 connected to a patient circuit 108. The patient circuit includes an inspiratory limb 112, an expiratory limb 116, and a patient limb 120. The inspiratory limb 112, expiratory limb 116 and patient limb 120 are interconnected to one another by a patient wye 124. The inspiratory 112 and expiratory 116 limbs respectively connect the patient wye 124 to a supply port 136 and a return port 140 provided by the ventilator 104. The patient supply limb 120 interconnects the patient wye 124 to a patient breathing apparatus 128. The ventilator 104 generally operates to provide a breathing gas to the inspiratory limb 112 for delivery to the patient breathing apparatus 128 via the patient wye 124 and the patient supply branch 120. The ventilator 104 may also receive exhaled air from the patient that is delivered to the return port 140 via the patient breathing apparatus 128, the patient supply limb 120, the patient wye 124, and the expiratory limb 116. The ventilator 104 may include a supply sensor 138 and a return sensor 142 to monitor the supplied breathing gas and the returned gas, respectively. Sensors 138 and 142 may be flow and/or pressure sensors, including flow or pressure transducers. In accordance with embodiments of the present invention, information regarding the flow of gas detected by the supply 138 and return 142 flow transducers is provided to a controller 132.

In addition, the ventilator 104 includes user input 144 and user output 148 facilities. In general, the user input 144 receives input from a user, such as a clinician, respiratory therapist, or other medical professional, related to controlling the operation of the ventilator 104. The user output 148 provides information to a user regarding the operational status of the ventilator 104, and may include any alarm conditions.

The breathing gas supply 152 is operated at the direction of the controller 132, and includes the mechanical components used to control the composition and flow characteristics according to which breathing gas is supplied to a patient. In accordance with embodiments of the present invention, the breathing gas supply 152 is not limited to any particular type of breathing gas supply. Examples of a breathing gas supply 152 include piston and/or bellows based air delivery systems or air delivery systems comprising turbines. The breathing gas supply 152 may additionally include pressure regulating valves. For example, pressure regulating valves may be used in connection with a mechanism for compressing air included in the breathing gas supply 152, such as a piston or turbine. In accordance with other embodiments, the breathing gas supply 152 provides pressure regulating valves that are used to control the flow of a gas or gasses provided by sources of pressurized gas that are external to the ventilator 104, such as when the ventilator 104 receives pressurized air and/or oxygen from centralized sources through wall outlets. In some embodiments, pressure regulating valves include proportional solenoid valves.

Breathing gas from the breathing gas supply 152 may be provided to the patient circuit 108 by the supply port 138.

The supply flow sensor or transducer 138 provides information regarding the flow of breathing gas that is being output by the ventilator 104 through the supply port 136. This flow information is passed back to the controller 132, to provide the controller 132 with feedback regarding the flow actually provided from the supply port 136 of the ventilator 104 to a patient. The return port flow sensor or transducer 142 monitors the flow of exhaled air from a patient that is received at the return port 140 of the ventilator 104. The information regarding the flow returned to the ventilator 104 from the patient circuit 108 is provided to the controller 132, which allows the controller 132 to perform various monitoring activities. These monitoring activities can include detecting the connection status of a patient.

The user input 144 generally functions to receive control commands from a user regarding the operation of the ventilator 104. Accordingly, the user input 144 can include one or more devices, such as a keyboard, a numeric keypad, a pointing device operated in connection with a display device, a touch screen interface and/or a microphone for receiving spoken commands. The user input 144 may additionally or alternatively include buttons or switches, either physical or virtual, that are dedicated to the control of specific ventilator 104 functions.

The user output 148 may comprise one or more devices that are operable to providing human perceptible output signals. Accordingly, examples of user output devices 148 include visual displays, indicator lamps, or audible signals. In addition, a user output 148 may include a device provided separately from or external to the ventilator 104. For instance, the user output 148 may comprise a communication interface provided as part of the ventilator 104 that provides a signal that is communicated to a user communication endpoint, such as a cellular telephone, pager or personal computer that causes the user endpoint to provide a human perceptible signal.

Figure 2:
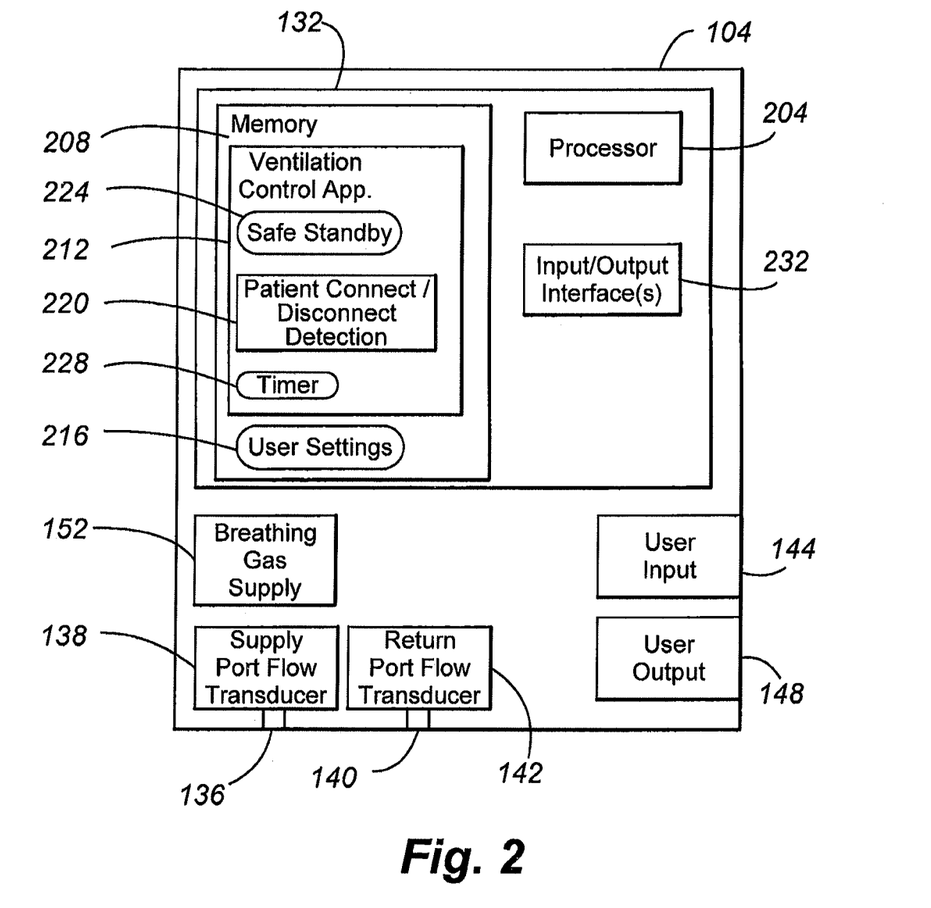
FIG. 2 is a block diagram depicting components of a ventilator providing a safe standby mode in accordance with embodiments of the present invention.

FIG. 2 is a block diagram depicting components of a ventilator 104 that provides a safe standby mode in accordance with embodiments of the present invention. As shown in FIG. 2, the ventilator 104 controller 132 may comprise a number of separate or integrated components. These components may include a processor 204 that is operable to execute program code, instructions or firmware related to the operation of the ventilator 104. The processor 204 may therefore comprise a general purpose programmable processor, an application specific integrated circuit or other processor. The code or instructions executed by the processor 204 may be stored in memory 208. The memory 208 generally comprises one or more solid state memory devices. Alternatively or in addition, the memory 208 may include other types of data storage devices, such as magnetic or optical storage devices. In general, at least some of the memory 208 is non-volatile, to allow for the long term storage of operating instructions for execution by the processor 204. Such instructions may include a ventilation control application 212. In addition, the memory 208 may be used to store user settings 216, for example entered in connection with use of the ventilator 104 to provide breathing gas to a particular patient.

The ventilation control application 212 generally controls the operation of the ventilator 104 in providing a breathing gas to a patient. Accordingly, this may include controlling the breathing gas supply 152 such that breathing gas having desired composition and flow characteristics is provided to the patient. In addition, the ventilation control application 212 may implement various sub-functions of the ventilator 104, such as a patient connect/disconnect detection function 220, a safe standby mode function 224, and the implementation of one or more timers 228 that may be set and monitored in connection with the execution of other functions. The user settings 216 generally include operating parameters entered by a user that relate to controlling the composition and flow characteristics of the breathing gas supplied to a patient, and any other user configurable operating parameters.

The controller 132 may also include one or more input/output interfaces 232. The input/output interfaces 232 operatively connect the controller 132 to other components of the ventilator 104. Accordingly, examples of input/output interfaces 232 may include communication bus or network interfaces, and/or dedicated input or output signal lines. In accordance with embodiments of the present invention, the controller 132 may be provided as a set of discrete components. Alternatively, the controller 132 may comprise a fully or partially integrated controller device.

In accordance with embodiments of the present invention, the user input 144 and user output 148 may operate in association with the ventilation control application 212 executed by or running on the processor 204 to provide a graphical user interface (GUI). Accordingly, a user may interact with the ventilator 104 by making selections and receiving information through a GUI provided by the ventilator 104. Alternatively or in addition, dedicated control inputs and outputs, such as switches, buttons, indicator lamps and audible alarms may be provided.

Figure 3A:
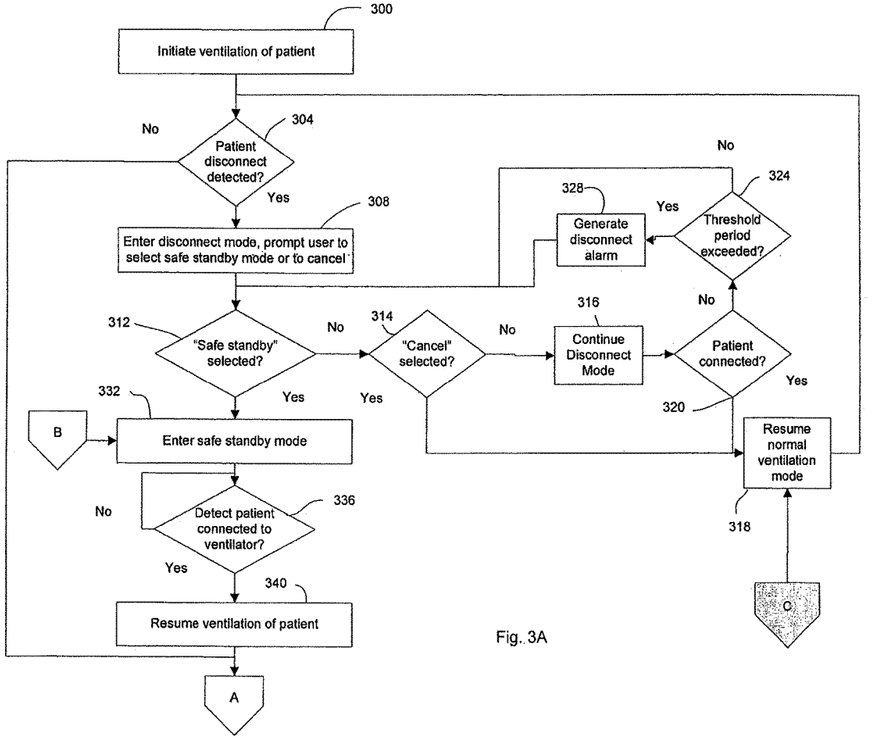
FIGS. 3A-3B present a flow chart depicting aspects of the operation of a ventilator providing a safe standby mode in accordance with embodiments of the present invention.
Figure 3B:
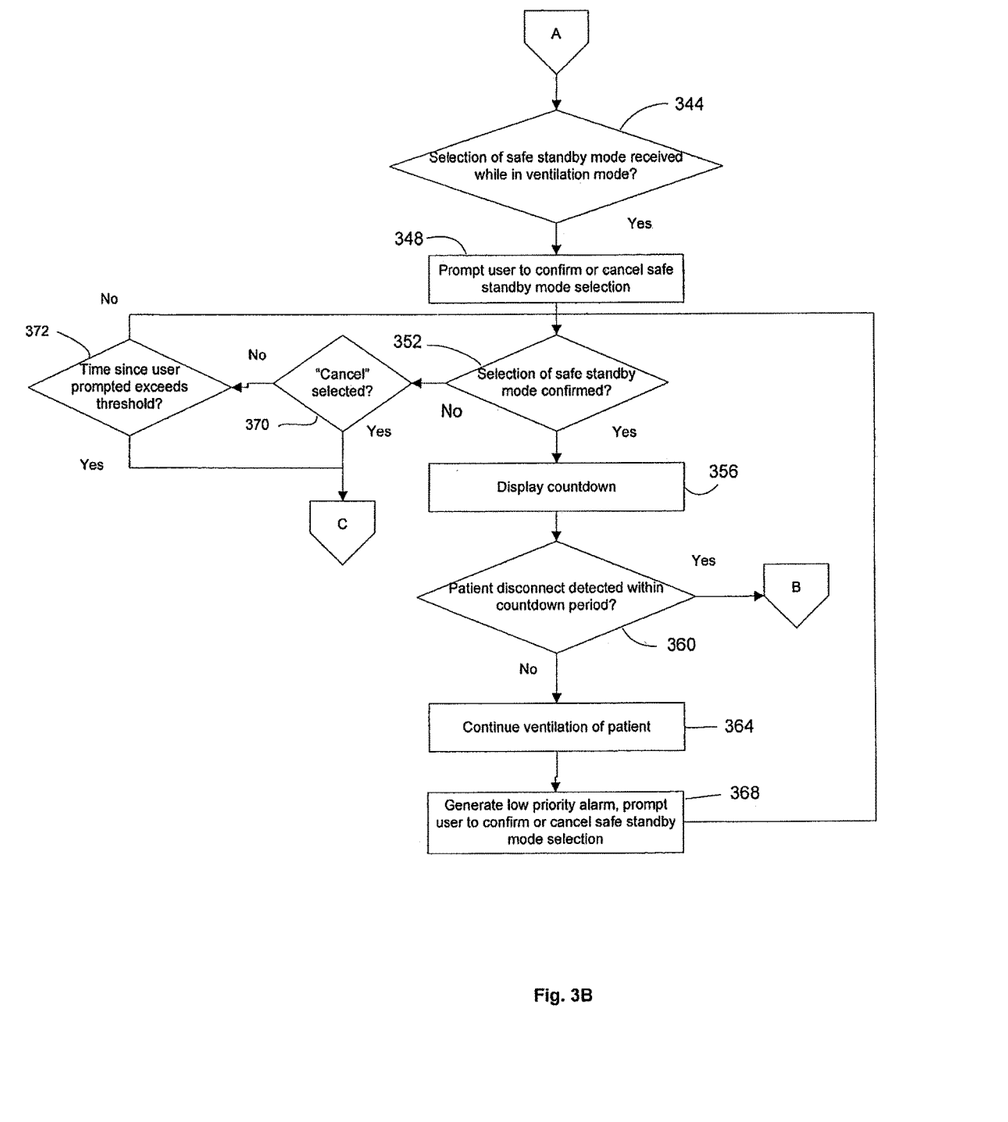

FIGS. 3A and 3B provide a flow chart depicting aspects of the operation of a ventilator 104 with a safe standby mode in accordance with embodiments of the present invention. Starting at step 300, ventilation of a patient is initiated. While the patient is being ventilated, the controller 132 may monitor the patient circuit 108 to determine whether the patient has become disconnected from the ventilator 104 (step 304). If it is determined that the patient has become disconnected from the ventilator 104, a disconnect mode is entered, and the user is prompted to select a safe standby mode or to cancel (step 308). For example, the following message may be displayed by the GUI of the ventilator 104:

Do you want to enable SAFE STANDBY?
[YES] [CANCEL]

At step 312, a determination as to whether a safe standby mode has been selected. If the safe standby mode has not been selected, a determination is made as to whether the "cancel" button has been selected (step 314). If "cancel" has been selected, the normal ventilation mode is resumed (step 318), and the process returns to step 304.

If "cancel" is not selected, the disconnect mode is continued (step 316). In the disconnect mode, the ventilator 104 does not provide breathing gas through the supply port 136 with the flow characteristics applied while in the ventilation mode. Instead, gas is supplied at a greatly reduced rate. As can be appreciated by one of skill in the art, by providing gas at a reduced rate through the supply port 136, the chance that microorganisms or other dangerous substances might be aerosolized and sprayed out of the patient circuit 108 is reduced. For example, whereas the ventilator 104 might supply breathing gas at flows of one hundred and fifty to two hundred (150-200) liters per minute during normal ventilation, in the disconnect mode gas is supplied at a rate of three (3) liters per minute. Providing some gas, even at a reduced flow, allows the ventilator 104 to monitor whether the patient has been reconnected. In particular, if a flow (or certain pressure) is detected at the return port 140 by the return port transducer 142, it may be taken as an indication that a patient has been reconnected, and normal ventilation may resume. Accordingly, while the ventilator 104 is in the disconnect mode, a check may be performed continually to determine whether the disconnect status has been resolved by connecting a patient to the ventilator (step 320). If it is determined that a patient has been connected to the ventilator 104, the normal ventilator mode is resumed (step 318).

If a connection to the patient is not detected at step 320, a determination may be made as to whether the period of time that the ventilator 104 has been in the disconnect mode exceeds some threshold period (step 324). As an example, the threshold period may be defined or selected to be five (5) seconds. If the threshold period of time has been exceeded, a high priority disconnect alarm is generated (step 328). After generating the alarm or after determining that the threshold period of time has not been exceeded, the process may return to step 312.

If it is determined at step 312 that a safe standby mode has been selected, the safe standby mode is entered (step 332). In the safe standby mode, the ventilator 104 is powered on and all settings entered by the user are maintained. However, in the safe standby mode breathing gas is not supplied at normal rates of ventilation. Instead, gas is delivered from the supply port 138 at reduced rates in order to monitor whether a patient is connected to the ventilator 104 while the ventilator 104 is in the safe standby mode. That is, the same techniques that are used to determine whether a patient has been connected to the ventilator in the disconnect mode are used in the safe standby mode. However, the safe standby mode differs from the disconnect mode in that a disconnect alarm is not periodically generated. Therefore, the patient can remain disconnected from the ventilator indefinitely, without requiring the user to periodically take action to silence a disconnect alarm. At step 336, a determination is made as to whether a patient connection to the ventilator 104 has been detected. If the monitoring determines that the patient remains disconnected, monitoring for a connection to a patient is continued. If a connection to a patient is detected, the normal ventilation mode is resumed (step 340). When the normal ventilation mode is resumed, ventilation of the patient may be performed in accordance with the parameters previously set by the user.

As can be appreciated by the description provided herein, the safe standby mode provided by some embodiments of the present invention automatically resumes the supply of a breathing gas according to previously selected flow characteristics if the ventilator 104 detects that the patient has been reconnected to the ventilator 104. This is in contrast to conventional ventilator standby modes, in which no automatic restart of ventilation is provided if the patient is reconnected to the ventilator. In addition, no disconnect alarm is sounded in the safe standby mode of embodiments of the present invention.

In some embodiments, after ventilation of the patient has been resumed at step 340, or if a patient disconnect has not been detected at 304, a determination may be made as to whether a selection of the safe standby mode has been received from a user while the ventilator 104 is in the normal ventilation mode (step 344) (see FIG. 3B). A safe standby mode can be selected by a user through, for example, a menu selection entered through the ventilator graphical user interface. If a selection of the safe standby mode has been received, the user is prompted by the ventilator 104 to confirm or cancel the safe standby mode selection (step 348). For example, the following message may be displayed by the GUI of the ventilator 104:

Do you want to enable SAFE STANDBY?
(You will have 5 seconds to disconnect patient)
[YES] [CANCEL]

A determination is then made as to whether the user has confirmed or canceled the safe standby mode selection (step 352). If the user selects YES to confirm, the ventilator 104 will display a countdown) (step 356). A determination is then made as to whether a patient disconnect has been detected within the countdown period (step 360). The countdown period may be a set period of time, for example, five (5) seconds, seven (7) seconds, ten (10) seconds, or the like. In alternative embodiments, the duration of the countdown period may be based on the respiration rate. For example, the countdown may last for a period of time equal to one full breath, two full breaths, or the like. Other methods of establishing a desired countdown period are possible within the scope of the present invention. As described previously, detection of a patient connection to the ventilator may be performed by monitoring whether a return flow is sensed by the return flow transducer 142 of the ventilator 104. If a patient disconnect is not detected within the countdown period, ventilation of the patient is continued (step 364). In addition, a low priority alarm may be generated, and/or the user may be further prompted to confirm or cancel the safe standby mode (step 368). For example, the following may be displayed by the ventilator GUI:

Patient Disconnect has taken too long
Do you still want to enable SAFE STANDBY?
(You will have 5 seconds to disconnect patient)
[YES] [CANCEL]

The process may then return to step 352 to determine whether the user has confirmed or canceled the safe standby mode selection. In accordance with embodiments of the present invention, ventilation of the patient is also continued if a selection of a safe standby mode is not received while the ventilator 104 is in the ventilation mode, or if the user fails to confirm a selection of the safe standby mode.

If it is determined at step 360 that the patient has been disconnected within the countdown period, the process proceeds to step 332, in which the safe standby mode is entered.

If it is determined at step 352 that the user has not confirmed entry into the safe standby mode, a determination may be made as to whether the user has canceled the safe standby mode selection (step 370). If the selection of the safe standby mode has been canceled, the process proceeds to step 318, and normal ventilation is resumed. If the user has not canceled the selection of the safe standby mode, a determination may be made as to whether a threshold time period since the user was prompted to confirm or cancel the safe standby mode exceeds some threshold amount (step 372). If the threshold time period has elapsed without receiving an entry from the user, normal ventilation may be resumed (step 318). If the threshold time has not been exceeded, the process may return to step 352 to monitor for a user selection.

In addition, a user may choose to discontinue ventilation at any time. If ventilation has not been discontinued, the process may return to step 304. If ventilation has been discontinued the process may end. Also, although processes that may be performed by a ventilator in accordance with embodiments of the present invention have been described in connection with steps that are performed in series, it should be appreciated that embodiments of the present invention are not limited to linear or serial operations. For example, the ventilator 104 may continuously monitor for any of a plurality of inputs from a user, for patient disconnect status, and/or for other inputs or conditions.

The foregoing discussion of the invention has been presented for purposes of illustration and description. Further, the description is not intended to limit the invention to the form disclosed herein. Consequently, variations and modifications commensurate with the above teachings, within the skill or knowledge of the relevant art, are within the scope of the present invention. The embodiments described hereinabove are further intended to explain the best mode presently known of practicing the invention and to enable others skilled in the art to utilize the invention in such or in other embodiments and with various modifications required by the particular application or use of the invention. It is intended that the appended claims be construed to include alternative embodiments to the extent permitted by the prior art.

What is claimed is:

1. A ventilator comprising:
   a processor; and
   a memory storing computer-readable instructions that when executed by the processor cause the ventilator to:
   receive an indication to initiate a standby mode;
   receive a confirmation of the indication to initiate the standby mode;
   initiate the standby mode, comprising:
      disable at least one patient disconnect alarm;
      discontinue normal ventilation of a patient;
      determine whether disconnection of the patient from the ventilator occurs within a period of time; and
      based on the determination, perform one of: resuming normal ventilation of the patient or monitoring for reconnection of the patient to the ventilator.

2. The ventilator of claim 1, further comprising:
   in response to determining that disconnection of the patient occurs within the period of time, monitoring for reconnection of the patient to the ventilator.

3. The ventilator of claim 2, the computer-readable instructions when executed by the processor further causing the ventilator to:
   detect reconnection of the patient to the ventilator; and
   automatically resume normal ventilation of the patient.

4. The ventilator of claim 3, the computer-readable instructions when executed by the processor further causing the ventilator to:
   store ventilator settings for use in normal ventilation; and
   automatically resume normal ventilation based on the stored ventilator settings.

5. The ventilator of claim 1, further comprising:
   in response to determining that disconnection of the patient does not occur within the period of time, resuming normal ventilation of the patient.

6. The ventilator of claim 1, wherein discontinuing normal ventilation of the patient comprises:
   supplying a gas at a rate less than a rate for normal ventilation.

7. The ventilator of claim 1, the computer-readable instructions when executed by the processor further causing the ventilator to:
   provide a prompt for confirmation of the indication to initiate the standby mode.

8. A ventilator system comprising:
   a user interface communicatively coupled to a controller, the user interface receiving:
      a selection of a standby mode, and
      a confirmation of the standby mode selection;

a breathing gas supply, the breathing gas supply interconnected to and operated in response to instructions from the controller; and the controller communicatively coupled to the user interface and the breathing gas supply, the controller in response to the standby mode selection and the confirmation of the standby mode selection, operative to:

disable at least one patient disconnect alarm;

detect disconnection of a patient from the ventilator within a period of time; and discontinue normal ventilation of the patient.

9. The ventilator system of claim 8, wherein discontinuing normal ventilation of the patient comprises:

supplying breathing gas at a rate less than a rate for normal ventilation.

10. The ventilator system of claim 8, further comprising:

providing, by the user interface, a prompt for confirmation of the standby mode selection.

11. The ventilator system of claim 8, the controller further operative to:

monitor for reconnection of the patient to the ventilator.

12. The ventilator system of claim 8, the controller further operative to:

detect reconnection of the patient to the ventilator; and automatically resume normal ventilation of the patient.

13. The ventilator system of claim 12, the controller further operative to:

store ventilator settings for use in normal ventilation; and automatically resume normal ventilation based on the stored ventilator settings.

14. A method implemented by a ventilator, the method comprising:

receiving an indication to initiate a standby mode;

receiving a confirmation of the indication to initiate the standby mode;

initiating the standby mode, comprising:

disabling at least one patient disconnect alarm;

detecting disconnection of a patient from the ventilator; and discontinuing normal ventilation of the patient.

15. The method of claim 14, further comprising:

monitoring for reconnection of the patient to the ventilator.

16. The method of claim 14, further comprising:

determining, while in the standby mode, that the patient is connected to the ventilator; and automatically resuming normal ventilation of the patient.

17. The method of claim 14, further comprising:

detecting reconnection of the patient to the ventilator; and automatically resuming normal ventilation of the patient.

18. The method of claim 17, further comprising:

storing ventilation settings for use in normal ventilation; and automatically resuming normal ventilation based on the stored ventilation settings.

19. The method of claim 14, wherein discontinuing normal ventilation of the patient comprises:

supplying breathing gas at a rate less than a rate for normal ventilation.

20. The method of claim 14, further comprising:

providing a prompt for confirmation of the indication to initiate the standby mode.

* * * * *